US010743832B2

(12) United States Patent
Schouten et al.

(10) Patent No.: US 10,743,832 B2
(45) Date of Patent: Aug. 18, 2020

(54) X-RAY BEAM SHAPING

(71) Applicant: KONINKLIJKE PHILIPS N.V., Eindhoven (NL)

(72) Inventors: Gerard Schouten, Nuenen (NL); Raoul Florent, Ville d'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 783 days.

(21) Appl. No.: 14/890,348

(22) PCT Filed: May 13, 2014

(86) PCT No.: PCT/EP2014/059734
§ 371 (c)(1),
(2) Date: Nov. 10, 2015

(87) PCT Pub. No.: WO2014/184179
PCT Pub. Date: Nov. 20, 2014

(65) Prior Publication Data
US 2016/0073999 A1 Mar. 17, 2016

(30) Foreign Application Priority Data
May 13, 2013 (EP) .................................... 13305601

(51) Int. Cl.
*A61B 6/00* (2006.01)
*A61B 6/06* (2006.01)
*A61B 6/12* (2006.01)

(52) U.S. Cl.
CPC ................. *A61B 6/547* (2013.01); *A61B 6/06* (2013.01); *A61B 6/12* (2013.01); *A61B 6/4441* (2013.01);
(Continued)

(58) Field of Classification Search
CPC .................................. A61B 6/547; A61B 6/06
See application file for complete search history.

(56) References Cited

U.S. PATENT DOCUMENTS 4,628,356 A * 12/1986 Spillman .............. G01N 23/043
348/E5.086
6,438,202 B1 8/2002 Olivera et al.
(Continued)

FOREIGN PATENT DOCUMENTS

| EP | 1380260 A1 | 1/2004 |
| JP | 04288146 A | 10/1992 |
| JP | 2012075782 A | 4/2012 |

OTHER PUBLICATIONS

"Xperience the future" Philips Allura Xper FD10/10 Functional description. pp. 1-31. https://www.philips.com/healthcare.
(Continued)

*Primary Examiner* — Rochelle D Turchen

(57) ABSTRACT

A medical X-ray imaging arrangement that includes an X-ray source, an X-ray detector, an X-ray beam manipulator device, a processor, and a memory unit. The X-ray beam manipulator device includes an adjustable X-ray beam diaphragm provided between the X-ray source and the X-ray detector. The beam diaphragm includes at least one movable X-ray beam-shaping element and at least one controllable actuator for moving the at least one beam-shaping element according to positioning data provided by the processor. The processor is configured to store positioning data of determined positions of the at least one beam-shaping element for determined attenuation configurations of the diaphragm, and to recall and supply the stored positioning data to the processor for activating the controllable actuator.

11 Claims, 14 Drawing Sheets

(52) U.S. Cl.
CPC .............. *A61B 6/461* (2013.01); *A61B 6/467* (2013.01); *A61B 6/504* (2013.01); *A61B 6/5211* (2013.01); *A61B 6/487* (2013.01)

(56) References Cited

U.S. PATENT DOCUMENTS

| | | | |
|---|---|---|---|
| 6,501,828 B1* | 12/2002 | Popescu ................... | A61B 6/06 378/145 |
| 2003/0219146 A1* | 11/2003 | Jepson ..................... | G06K 9/32 382/103 |
| 2004/0127789 A1 | 7/2004 | Ogawa | |
| 2006/0203966 A1 | 9/2006 | Mollus | |
| 2011/0110570 A1* | 5/2011 | Bar-Shalev ........... | G06T 11/005 382/131 |
| 2011/0182492 A1 | 7/2011 | Grass et al. | |
| 2013/0083895 A1 | 4/2013 | Umekawa et al. | |

OTHER PUBLICATIONS

Dick Stueve, "Management of pediatric radiation dose using Philips fluoroscopy systems DoseWise: perfect image, perfect sense", Pediatr Radiol (2006) 36, (Suppl 2): pp. 216-220, DOI 10.1007/s00247-006-0216-0.

* cited by examiner

X-RAY BEAM SHAPING

CROSS-REFERENCE TO PRIOR APPLICATIONS

This application is the U.S. National Phase application under 35 U.S.C. § 371 of International Application No. PCT/EP2014/059734/, filed on May 13, 2014, which claims the benefit of European Patent Application No. 13305601.0, filed on May 13, 2013. These applications are hereby incorporated by reference herein.

FIELD OF THE INVENTION

The present invention relates to manipulating an X-ray beam, and relates in particular to a medical X-ray imaging arrangement, to an X-ray imaging system, and to a method for X-ray image acquisition, as well as to a computer program element and a computer-readable medium.

BACKGROUND OF THE INVENTION

In X-ray imaging, for example for medical X-ray imaging, the generated X-ray beam may be manipulated, for example with respect to size and positioning. For imaging a selected region of interest of an object, shutters may be adjusted such that unnecessary radiation of the object, for example a patient, is avoided or at least reduced to a minimum. For example, US 2011/0182492 A1 relates to an angiographic image acquisition system and mentions an automatic adjustment of a collimator wedge for collimating an X-ray beam according to a segmented target structure or lesion. Besides automatic adjustment, also manual adjustment may be provided by the user; such manual adjustment may be time-consuming and requires attention of the user.

US 2004/0127789 A1 describes an X-ray diagnostic system that may be used for imaging the lower limb of an object. The system may perform a fluoroscopic pre-scan to obtain a body-axis directional image of the anatomy of interest. Imaging parameters may be set region by region in the body-axis direction, for example by an operator using a pointing device to set, for each imaging position, a desired size of the X-ray collimator. Thus, an examination protocol is defined that is used during the final imaging scan of the anatomy of interest.

SUMMARY OF THE INVENTION

There may be a need to provide a facilitated X-ray beam manipulation in particular during an interventional procedure.

The object of the present invention is solved by the subject-matter of the independent claims, wherein further embodiments are incorporated in the dependent claims. It should be noted that the following described aspects of the invention apply also for the medical X-ray imaging arrangement, the X-ray imaging system for medical imaging, and the method for X-ray image acquisition, as well as for the computer program element and the computer readable medium.

According to the present invention, a medical X-ray imaging arrangement is provided, that comprises an X-ray source, an X-ray detector, an X-ray beam manipulator device, a control unit, and a memory unit. The X-ray source and the X-ray detector are movable so as to achieve different imaging positions. The X-ray beam manipulator device comprises an adjustable X-ray beam diaphragm provided between the X-ray source and the X-ray detector, which diaphragm comprises at least one movable X-ray beam-shaping element and at least one controllable actuator for moving the at least one beam-shaping element according to positioning data provided by the control unit.

The control unit is arranged for determining positioning data representing positions of the at least one beam-shaping element for a configuration of the beam diaphragm for an imaging position and determining imaging configuration data corresponding to said imaging position. The memory unit is configured for storing the determined positioning data and the determined imaging configuration data.

The control unit is further arranged for i) comparing imaging configuration data corresponding to a current imaging position with the imaging configuration data stored in the memory unit; ii) recalling, from the memory unit, positioning data representing a configuration of the beam diaphragm associated with the current imaging position, and iii) activating the controllable actuator in accordance with the recalled positioning data.

This provides the advantage, that, for example, in a current imaging position being used during an interventional procedure, a configuration of the beam diaphragm may be stored together with data on the corresponding imaging position. The data may for example be stored by the user, and the respective positioning data can be used during the remainder of an interventional procedure, e.g. for further beam manipulating configurations or to restore the current configuration of the beam diaphragm when the current imaging position is resumed. Thus, the user can rely on previously acquired and stored configurations.

The "current" imaging position as understood herein refers to an imaging position that is used at a current step in the workflow of an interventional procedure, as determined by a user. That is, at any time during the procedure, when a user feels it is beneficial to store the beam diaphragm configuration that is set at that particular point in time, this is enabled by an imaging arrangement according to the invention.

According to an example, a user interface is provided to activate storing the positioning data and the image configuration data. Preferably, when an element of the user interface is activated, positioning data of a current configuration of the beam diaphragm i.e. the configuration of the beam diaphragm at the time of the user interaction, and the corresponding image configuration data of a current imaging position. i.e. a position of the X-ray source and X-ray detector at the time of the user interaction, is stored.

This provides the advantage that a facilitated way of achieving different positioning data sets is provided. The user can then later get back to these particular configurations.

Further, an advantage is that for a particular viewing direction and viewing type, for example, the user can also connect certain manipulation configuration and can use the same in connection at a later point in time.

According to an example, a user interface is provided to switch between different imaging modes, wherein the different imaging modes are at least partly connected with the positioning data of a particular beam diaphragm configuration actively stored by the user.

In particular, for one imaging position, the positioning data may include a plurality of data sets each representing a particular configuration of the beam diaphragm. In other words, for one imaging position, different diaphragm configurations may be stored, each preferably corresponding to a particular imaging mode.

This provides the advantage that, on one side, a user can differentiate between different imaging modes, for example between an overview and a detailed view, and, on the other side, the diaphragm configuration can be stored and connected therewith to facilitate the desired X-ray beam manipulation during different modes of viewing. That is, different diaphragm configuration may be stored for example for the overview and detailed view; when a user indicates to switch from a detailed view to an overview mode, positioning data representing the diaphragm configuration in that mode is recalled from the memory unit and the at least one beam-shaping element is activated accordingly.

According to an example, the at least one beam-shaping element is a shutter element for attenuating an X-ray beam with a first degree of attenuation. The at least one beam-shaping element may in addition or alternatively be a wedge element for attenuating an X-ray beam with a second degree of attenuation.

For example, the shutter element may be provided for limiting the beam size and shape. In a further example, the wedge element can be provided for adapting areas in terms of attenuation, for example for providing preconfigured image data for facilitated image data processing. In other words, a wedge may be provided that leads to an attenuation effect in an increased or decreased manner and thus avoids sharp edges.

According to the invention, an X-ray imaging system is provided for medical imaging, comprising an X-ray imaging device, a display device, and an object support device. The X-ray imaging device is provided as a medical X-ray imaging arrangement according to one of the above-mentioned examples. The display device is configured to display image data of an object arranged on the object support device, wherein the image data is provided by the X-ray detector.

According to an example, an attenuation position indicator is displayed overlaid to an un-attenuated image region, which attenuation position indicator indicates a stored attenuation scheme.

According to an example, the control unit is configured to detect a variation of the geometric relation of the X-ray imaging arrangement and/or the object under examination. The control unit is further configured generate adapted positioning data from stored positioning data in accordance with the detected variation, and to supply the adapted positioning data to the at least one controllable actuator.

In an example, when the at least one beam-shaping element is re-called in a previously stored position, the control unit is further configured to automatically move the X-ray source and the detector to the corresponding imaging position.

According to an example, the control unit comprises an image processor that is configured for object detection in a provided sequence of images for the detection of the variation of the geometric relation. The control unit comprises a heuristic module with a number of heuristic layers containing different scenarios. The different scenarios comprise predetermined activatable measures affiliated with the recall of stored positioning data.

According to an example, the control unit comprises an image detection module to detect predetermined elements in the image data relating to a predetermined interventional procedure. The control unit comprises a store-recall activation module to activate storing and recalling of an attenuation configuration depending on the image content and activated imaging mode.

According to the invention, a method for X-ray image acquisition is provided, comprising the following steps:
a) moving at least one movable X-ray beam-shaping element of an adjustable X-ray beam diaphragm of an X-ray beam manipulator device of a medical imaging arrangement into a first position of a first attenuation configuration; and acquiring X-ray image data in a first imaging mode;
b) storing positioning data of the position of the at least one beam-shaping element and imaging configuration data in a memory unit;
c) moving at least one movable X-ray beam-shaping element into a second position of a second attenuation configuration; and acquiring X-ray image data in a second imaging mode,
d) comparing imaging configuration data for a current imaging position with stored imaging configuration data; and
e) recalling stored positioning data for the current imaging position and supplying the recalled positioning data to a control unit for activating the controllable actuator and moving the at least one movable X-ray beam-shaping element into the first position of the first attenuation configuration; and acquiring X-ray image data in the first imaging mode.

According to the invention, a store-and-recall feature for shutters and wedges is provided in an example. The store-and-recall feature facilitates the use of shutters and wedges during a clinical case, in particular an interventional procedure. During an interventional procedure, various beam diaphragm configurations may be used in different imaging positions and, optionally, in different imaging modes. According to the invention, these configurations may be stored by a user over the course of the procedure, together with the corresponding imaging positions and optionally imaging mode.

Then, the correct diaphragm configuration that is actually required at the subsequent step in the interventional workflow may be quickly recalled from the memory unit, whereby the at least one beam-shaping element is automatically actuated in accordance with the recalled data.

For example, during an interventional procedure of placing coils in a brain aneurysm, or placing stents in a coronary artery, the clinical user may have to switch between different imaging positions and/or between a detailed view, for example viewing a coil in an aneurism in the brain or a stent in a coronary artery, and an overview, for example viewing an angiogram for evaluating the lumen and blood flow beyond an implanted device. In accordance with the present invention, there is no need for the user to attempt different placements of shutters and wedges in trying to find a similar beam diaphragm configuration as was used in a respective imaging mode and/or position before. Thus, the invention may significantly shorten the length of the procedure, thereby achieving dose reductions.

The shutter and wedge store-and-recall function may be provided directly by user interaction, in which case a button can be used on a user interface device for storing and recalling. In a further example, fully automatic application can be provided by applying smart image processing combined with heuristics.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
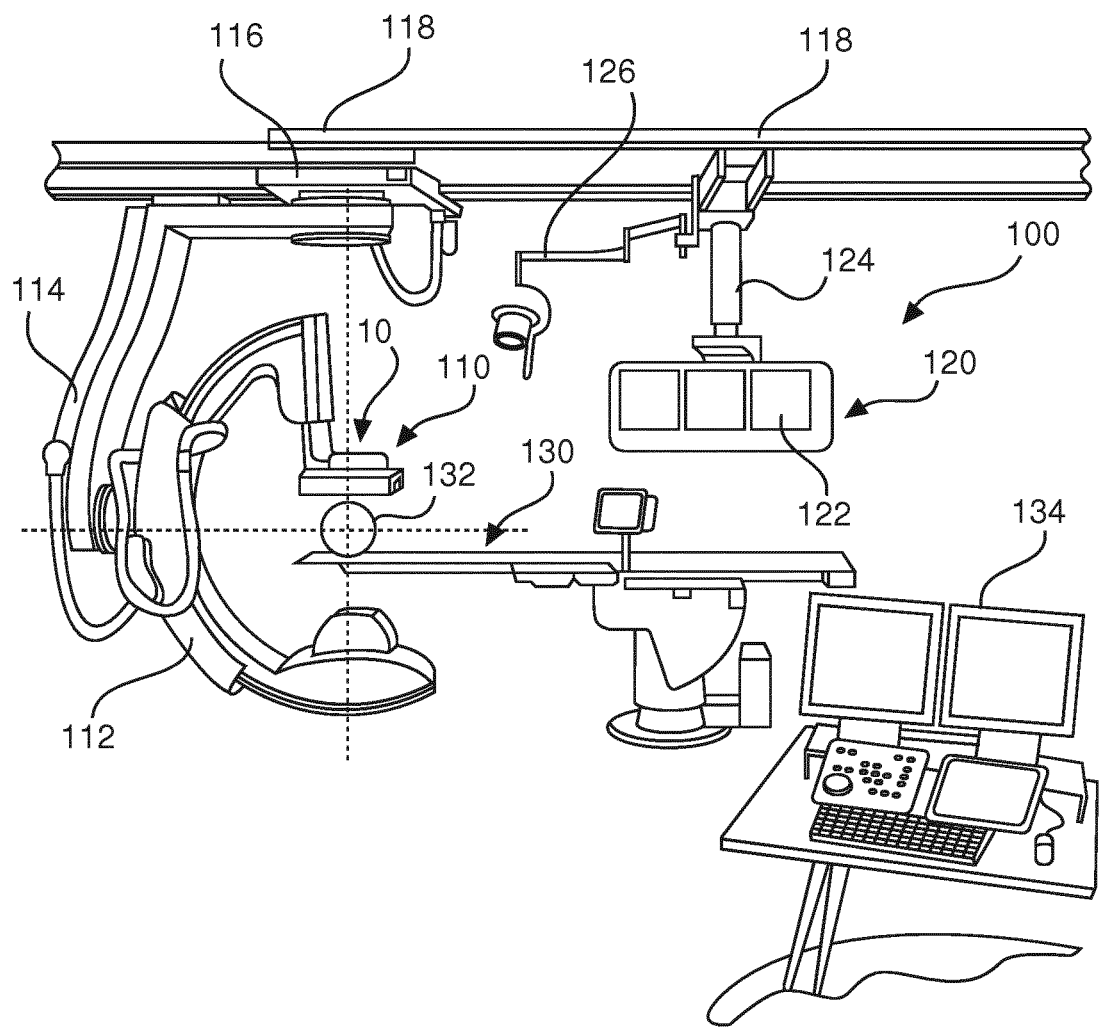
FIG. 1 shows an example of a medical X-ray imaging system in a schematic perspective setup.

FIG. 1 shows an X-ray imaging system 100 for medical imaging. The system comprises an X-ray imaging device 110, a display device 120, and an object support device 130. The X-ray imaging device 110 may be provided as a so-called C-arm system with a C-arm structure 112 for supporting X-ray source and detector. The C-arm 112 may be supported by a ceiling suspension 114, which is movably attached to a ceiling support system 116 to a ceiling 118. Alternatively, a floor mount for the C-arm may be used.

The display device 120 may comprise several display surfaces 122, for example suspended by a support 124 from the ceiling 118. Further, also additional lighting equipment 126 may be provided in the vicinity. The object support device 130 may be a patient table. A circular structure 132 is indicating an object, for example a patient's head.

Still further, a control station 134 may be provided in data connection with the other components.

The X-ray imaging device 110 is provided as a medical X-ray imaging arrangement 10 according to one of the below described examples. The display device 120 is configured to display image data of an object arranged on the object support device 130, wherein the image data is provided by the X-ray detector.

It must be noted that FIG. 1 shows a C-arm system. However, also other types of X-ray imaging systems for medical imaging are provided, such as a CT system with a gantry and a rotating source/detector configuration. Further, also other types of X-ray imaging systems may be provided, for example fixed or partly fixed X-ray systems where the source and detector, or only one of the two is fixedly arranged. For example, also different types of patient support may be provided, for example a standing arrangement where a patient is standing in an upright manner, or a mammography system, and the like. For example, stand supports for chest imaging or breast support in relation with mammography may be provided.

Figure 2:
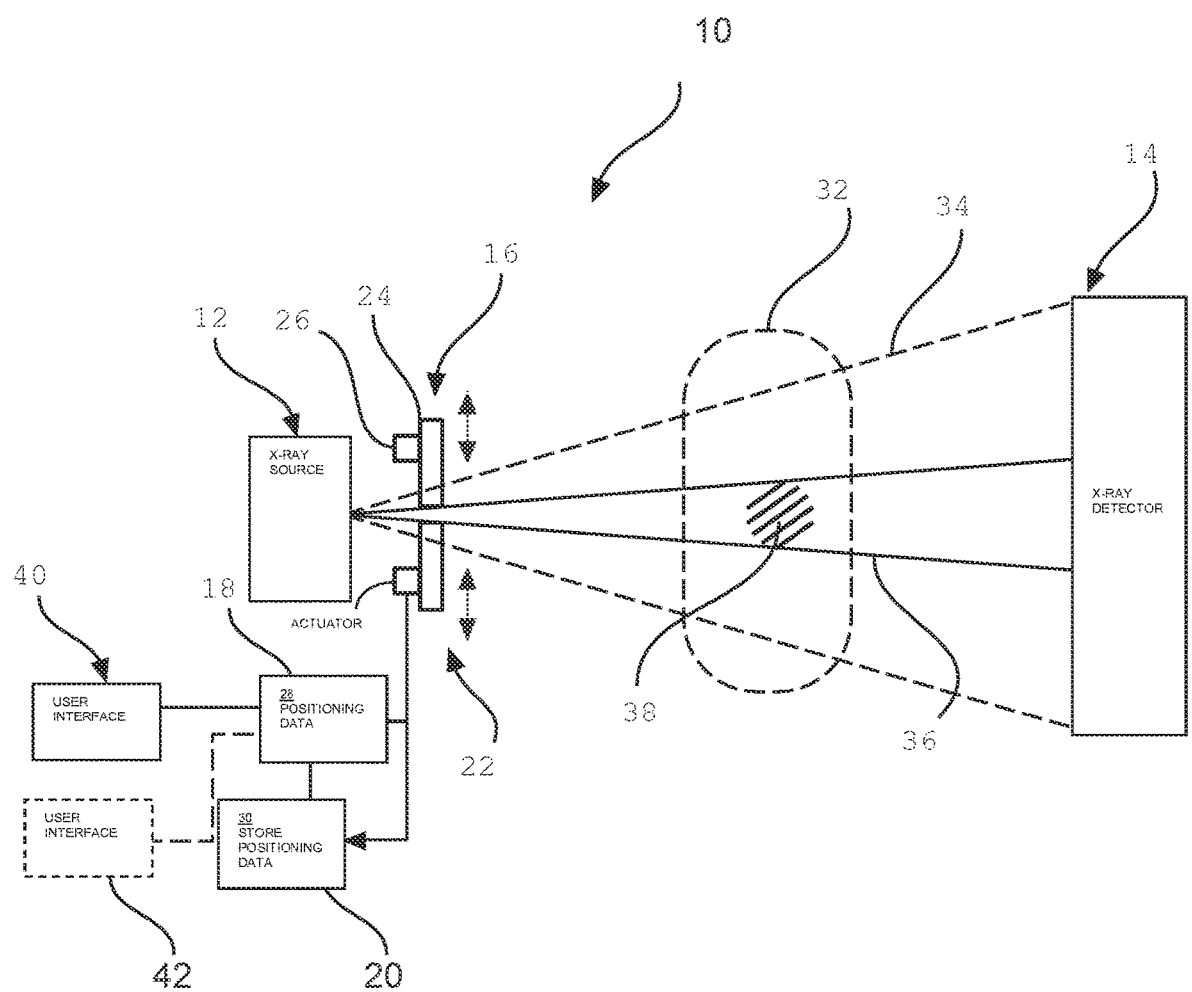
FIG. 2 shows an example of a medical X-ray imaging arrangement in a schematic cross-section of a first example.

FIG. 2 shows an example of a medical X-ray imaging arrangement 10, comprising an X-ray source 12, an X-ray detector 14, an X-ray beam manipulator device 16, a control unit 18, and a memory unit 20. The X-ray beam manipulator device 16 comprises an adjustable X-ray beam diaphragm 22 provided between the X-ray source 12, and the X-ray detector 14. The beam diaphragm 22 comprises at least one movable X-ray beam-shaping element 24 and at least one controllable actuator 26 for moving the at least one beam-shaping element 24 according to positioning data 28 provided by the control unit. The memory unit 20 is configured to store positioning data 30 of determined positions of the at least one beam-shaping element 24 for determined attenuation configurations of the diaphragm 22, and to recall and supply the stored positioning data to the control unit 18 for activating the controllable actuator 26. The memory unit further stores imaging configuration data for corresponding imaging positions. An object, indicated with dotted line 32 can be arranged between the adjustable X-ray beam diaphragm 22 and the X-ray detector 14. For example, the object is a patient.

The at least one beam-shaping element 24 is provided to be movable into an open position of the diaphragm (not shown in FIG. 2) where the at least one beam-shaping element 24 is arranged outside the X-ray beam, or non-limiting the X-ray beam to a maximum size, which maximum size is indicated with a first pair of dotted boundary lines 34. The at least one beam-shaping element 24 is also movable into an attenuation position, as shown in FIG. 2, where the at least one beam-shaping element 24 is arranged at least partly in the X-ray beam, providing a restricted beam size, as indicated with a pair of through lines 36, for example in order to radiate only a limited region of interest 38 of the object 32. The X-ray beam diaphragm 22 may also be referred to as an adjustable collimator. In an example, several attenuation positions are stored.

The beam-shaping element 24 is also referred to as X-ray beam-shaping element. The term "beam-shaping element" refers to an element or part that spatially restricts and attenuates the X-ray beam.

The term "positioning data" refers to data for the arrangement, i.e. adjustment or location of the beam-shaping element 24.

According to a further example, a user interface 40 is provided to activate storing positioning data of a current beam diaphragm configuration and corresponding imaging configuration data. The imaging configuration is assigned to the positioning data of the current beam diaphragm configuration. It must be noted that this user interface 40 is provided as an option. Therefore, although shown in combination with the other features mentioned above in relation with FIG. 2, the interface 40 may also be omitted in a further example.

The user interface may be provided as a memory and recall button for activating the storage of a current position and for reading stored positioning data from the memory unit and supplying the positioning data to the control unit. The term "configuration" refers to a positioning of the at least one beam-shaping element.

According to a further example, as a further option, the at least one beam-shaping element is adjustable by a user to achieve a user-adapted attenuated configuration. The interface is provided for activation of a storage of positioning data for the user-adapted attenuation configuration.

The adjustment of the at least one beam-shaping element may be supported by automatic adjustment based on image analysis provided by the control unit. The adjustment may be provided completely automatic.

According to a further example, a further user interface 42 is provided to switch between different imaging modes. The different imaging modes are at least partly connected with the positioning data of a particular beam diaphragm configuration actively stored by the user. That is, different sets of positioning data 30 may be stored for each imaging position, whereby each set of positioning data for example corresponds to a different one of the imaging modes.

It must be noted that the further user interface 42 is provided as an option, although shown in combination with the other features of FIG. 2. This is further supported by the indication of the further user interface 42 with dotted lines.

In a further example, the two user interfaces are combined, i.e. a user interface for activating the storing of the positioning data of a current beam diaphragm configuration is provided, which also serves for entering of commands to switch between different imaging modes.

For example, the user can store positioning data for a beam diaphragm configuration, e.g. a shutter configuration for detailed view, and can then change the beam diaphragm configuration, for example, move all shutters to an open, un-shuttered configuration for an overview. Following, the user can recall the stored configuration, e.g. for the detailed view. Thus, a change between "store" and "recall" is provided. For example, positions for different configurations of the beam diaphragm can be stored.

As indicated in FIG. 2, the at least one beam-shaping element can be a shutter element for attenuating an X-ray beam with a first degree of attenuation. The at least one beam-shaping element may also be a wedge element for attenuating an X-ray beam with a second degree of attenuation. The first and the second degree of attenuation may differ from each other. The term "shutter element" refers to an element that attenuates X-ray radiation with a continuous attenuation degree across the elements surface. The term "wedge element" refers to an element that attenuates X-ray radiation with a varying attenuation degree across the elements surface, for example an increasing degree of attenuation.

The at least one beam-shaping element may be a shutter element for attenuating an X-ray beam with a first degree of attenuation. In an example, the first degree of attenuation is provided such that in the first degree attenuated areas, information about an object is only rarely indicated in the detected image data. For example, the first degree of attenuation is provided as 90 percent attenuation. For example, the first degree of attenuation is provided as absorption such that X-ray radiation is not measured, or at least not visibly, by the detector in the respective areas.

The at least one beam-shaping element may be a wedge element for attenuating an X-ray beam with a second degree of attenuation. In an example, the second degree of attenuation is provided such that in the second degree attenuated areas, information about an object is indicated in the detected image data. For example, the second degree of attenuation is provided as approximately maximum 60 percent attenuation, for example 30 percent attenuation.

For better explanations, in the following, a clinical coiling procedure is described with reference to FIGS. 3A, 3B, 3C, and 3D. These Figures are line drawings schematically representing the original X-ray images in FIGS. 8A, 8B, 8C and 8D.

Usually, a coiling case starts with a diagnostic phase, in which one or more cerebral arteries are inspected. When an aneurism is found, a 3D angiogram is made. This may mark the end of the diagnostic phase. The 3D angiogram is used to determine the optimal projection for the treatment phase. In the treatment phase, devices, for example micro-catheter for delivering the coil wire, are maneuvered into the right position. Once this is done, the coiling process starts under fluoroscopy, see for example FIGS. 3A and 8A. From this point on, geometry and field of view of the system may stay the same, or at least essentially the same, for almost the entire intervention. To minimize dose, shutters and wedges might be placed around the devices leaving the insertion path open. For example, a fluoroscopy image 200 shows anatomical information 202, and a guide wire 204. A first degree of attenuation is provided by first attenuated areas 206, which are attenuated by wedges. A first type of line 208, for example a dotted line, indicates the respective geometric boundary line of the wedge. Further, a second type of attenuated area 210 is provided, for example as shutter attenuated areas. The respective limitation is indicated by a second type of line, for example a through line 212. As an example, the second type of attenuated area is provided on the right side and in the upper portion. In addition, the wedge-attenuated area 206 is provided in the lower right portion and the upper left portion. For example, the wedge-attenuated area 206 may overlap with the shutter-attenuated area 210.

This particular attenuation configuration may be stored.

Figure 3A:
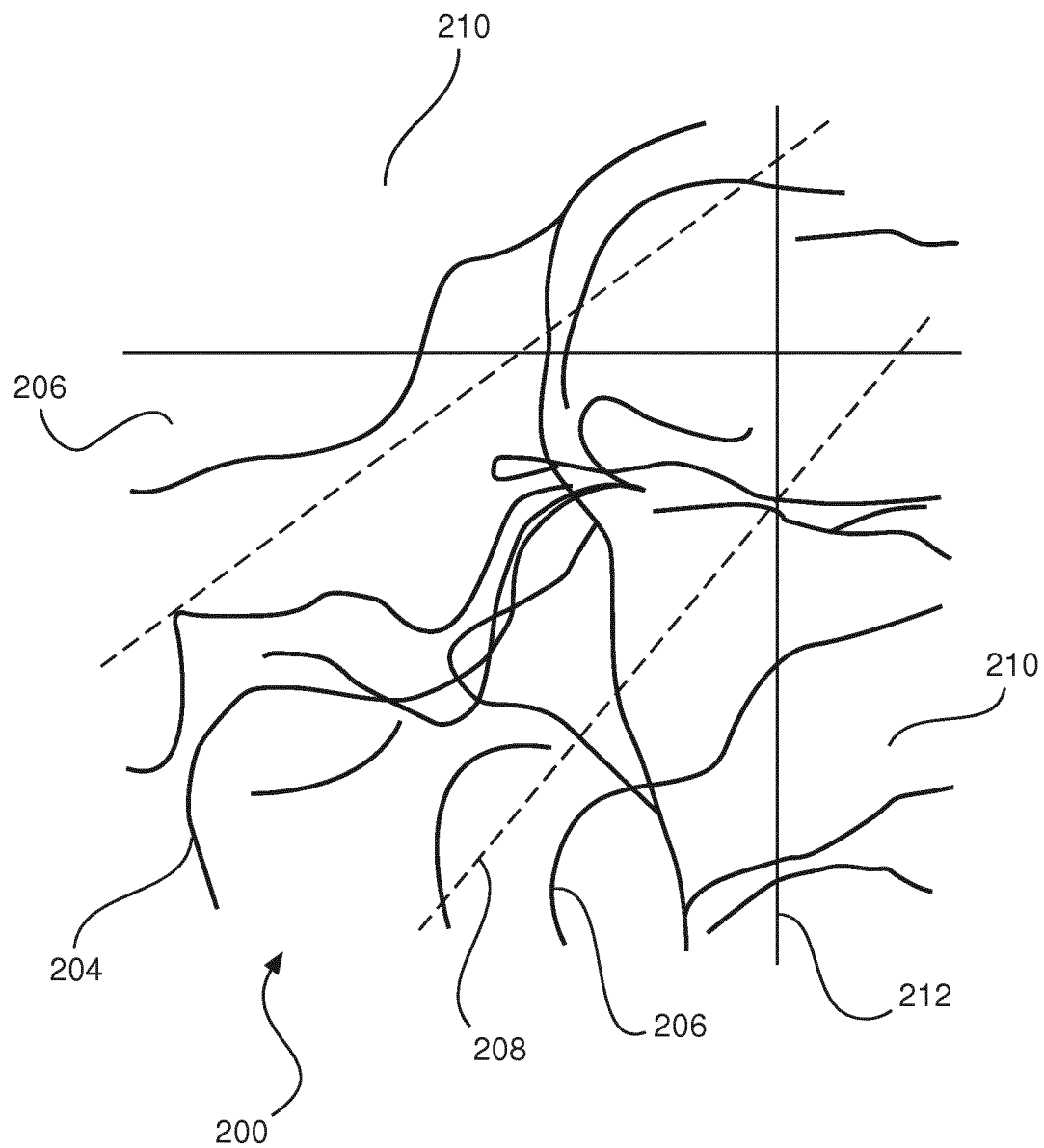
FIG. 3 shows examples of a displayed image for different situations during an interventional procedure in FIGS. 3A, 3B, 3C, and 3D.
Figure 3B:
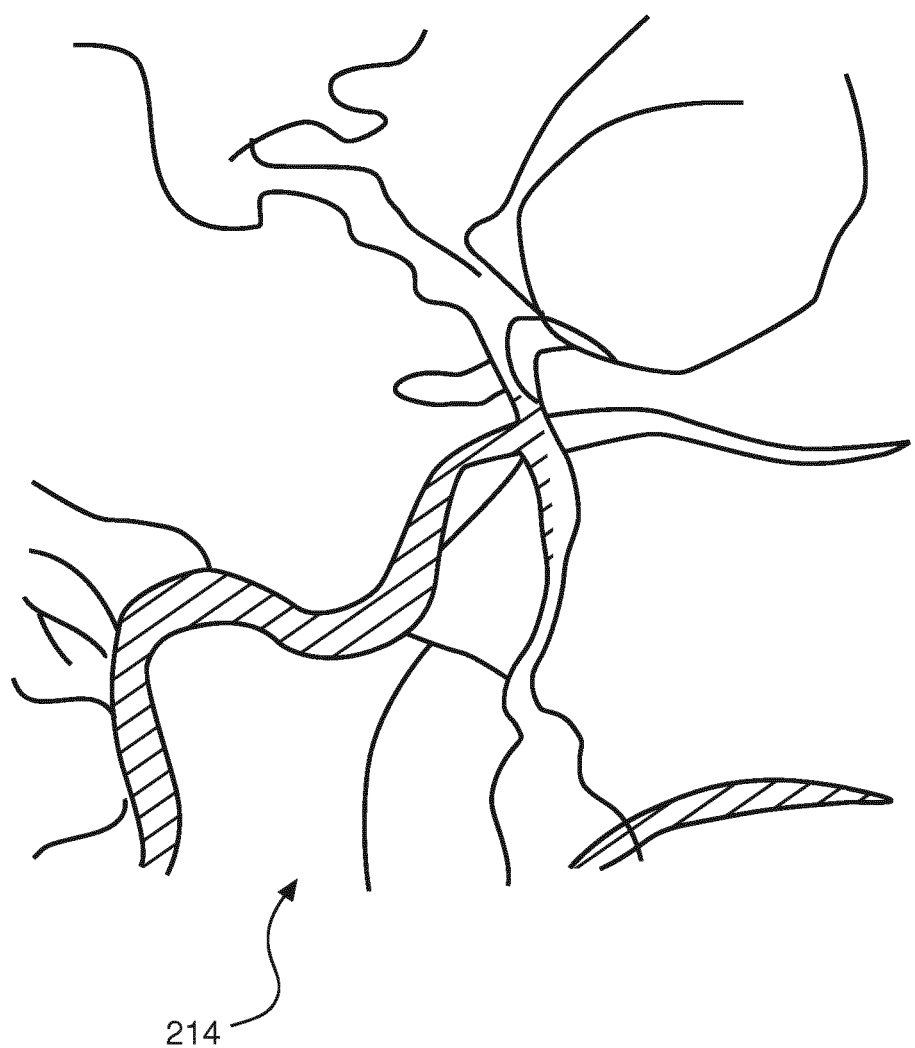
Figure 8A:
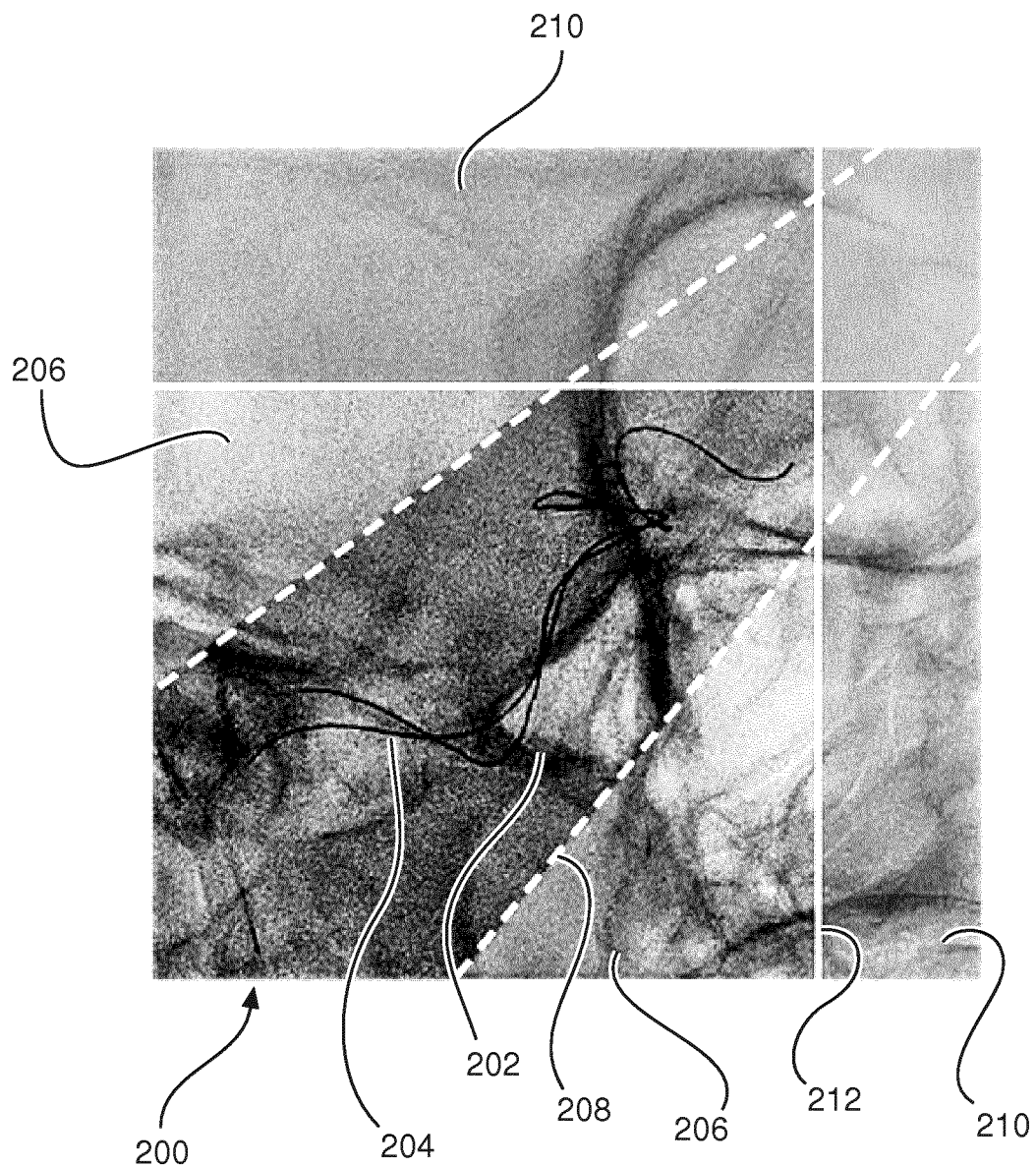
FIG. 8 shows photographic illustrations of FIG. 3, i.e. the illustrations in FIGS. 8A, 8B, 8C and 8D are related to FIGS. 3A, 3B, 3C, and 3D.
Figure 8B:
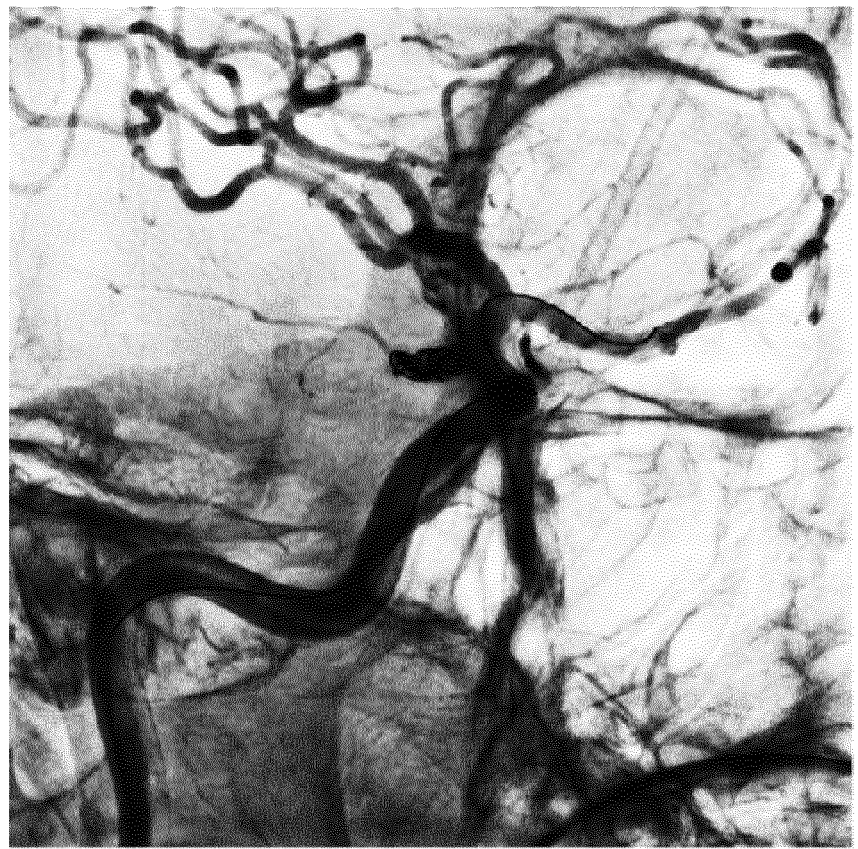

When the first coil wire is completely in the aneurism, it will be decoupled from the pusher wire. After that, the clinician makes an angiogram to check the blood flow. Here, the shutters and wedges are removed, because having an overview may be important in this particular situation. FIGS. 3B and 8B show an example of an angiogram 214, in which a vascular structure is shown. For generating the angiogram, there may be a need to change the imaging position, i.e. move the X-ray source and detector.

Depending on the outcome of the blood flow check, other coils might be pushed in under fluoroscopy using the same imaging position or a different, more suitable imaging position. After decoupling the second coil again, an angiogram may be made to evaluate the situation. This process is repeated until the clinician is satisfied, sometimes even up to six coils are used.

Figure 3C:
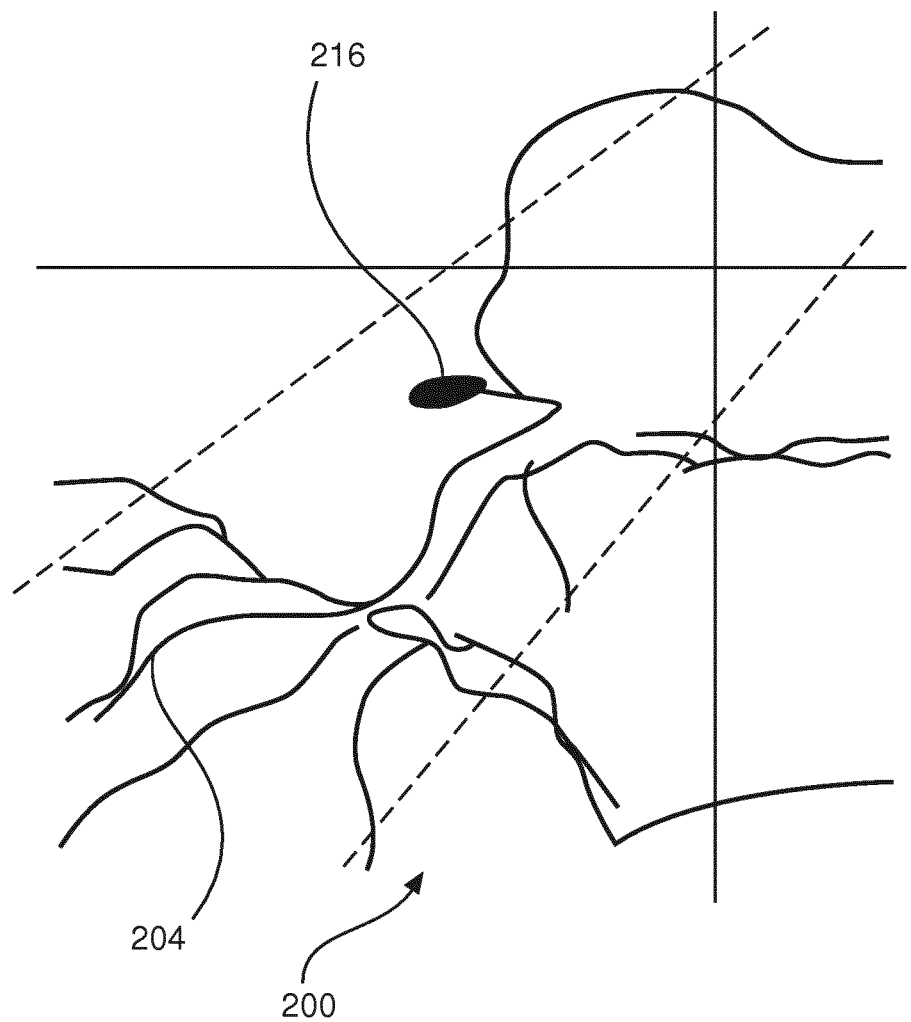
Figure 3D:
Figure 8C:
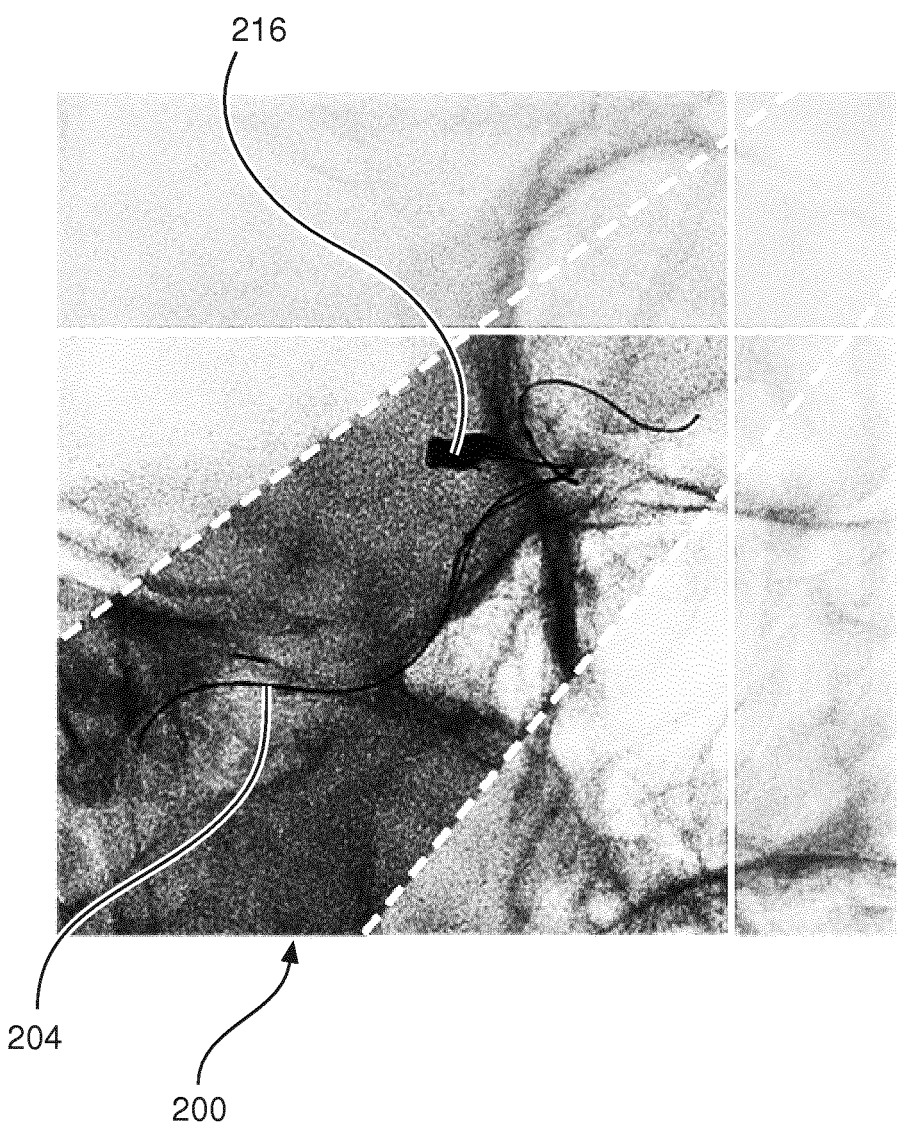

For example, FIGS. 3C and 8C show the delivering of the third coil in once again attenuated configuration. In addition to the guide wire 204, a coil 216 is shown. Further, an angiogram, shown in FIGS. 3D and 8D, indicated with reference character 218, may be made after placement of a further coil in the aneurism. For example, the geometry of the system and the patient stays the same during the different acquisitions.

Figure 8D:
Figure 8D:

In a further example, for each new coil delivery, as for example shown in FIGS. 3C and 8D, the actual imaging position may be compared to imaging positions stored in the memory unit and, if it matches one of the previously used positions, stored shutter and wedge configuration can be advantageously reused, i.e. recalled.

Figure 4:
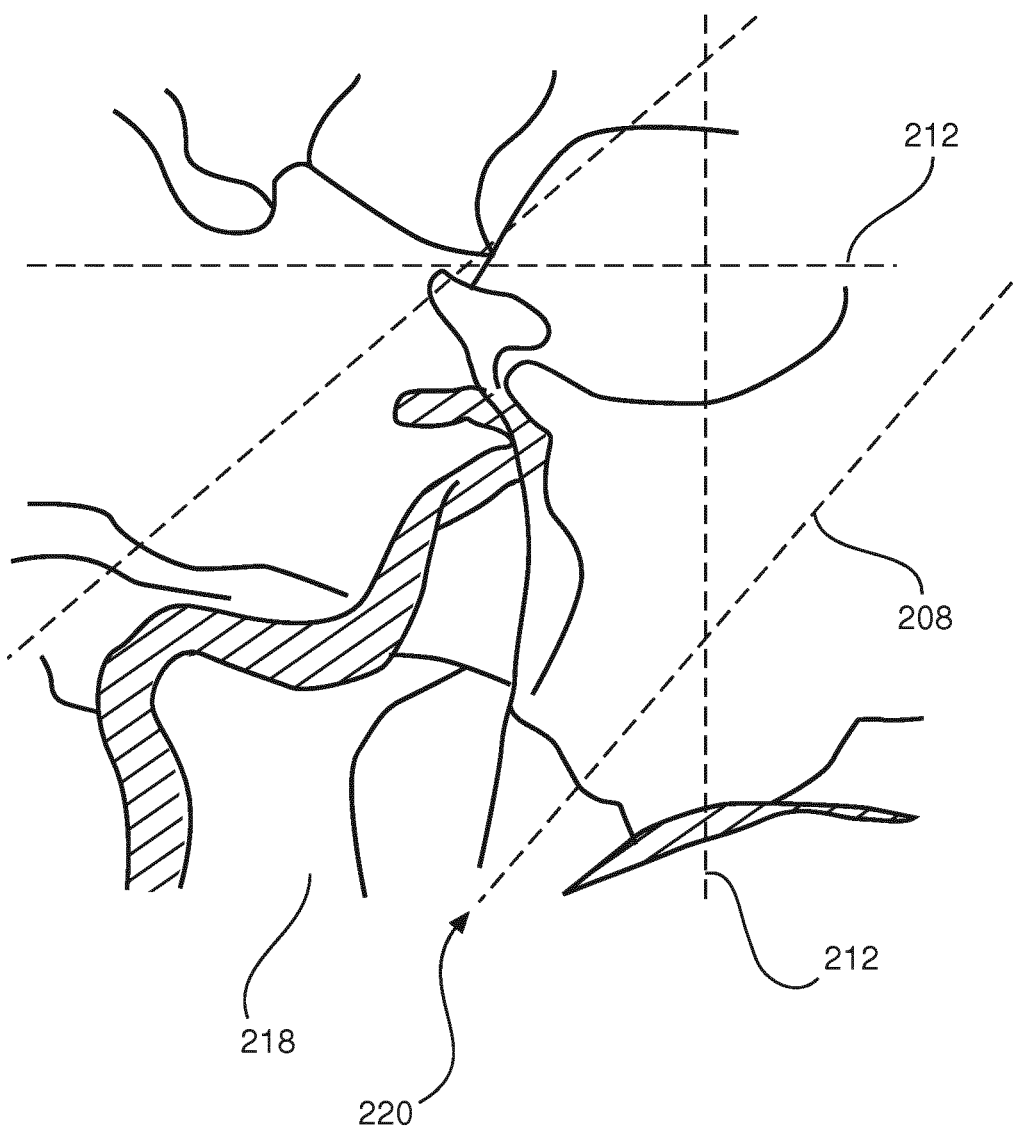
FIG. 4 shows a further example of a displayed image.
Figure 9:
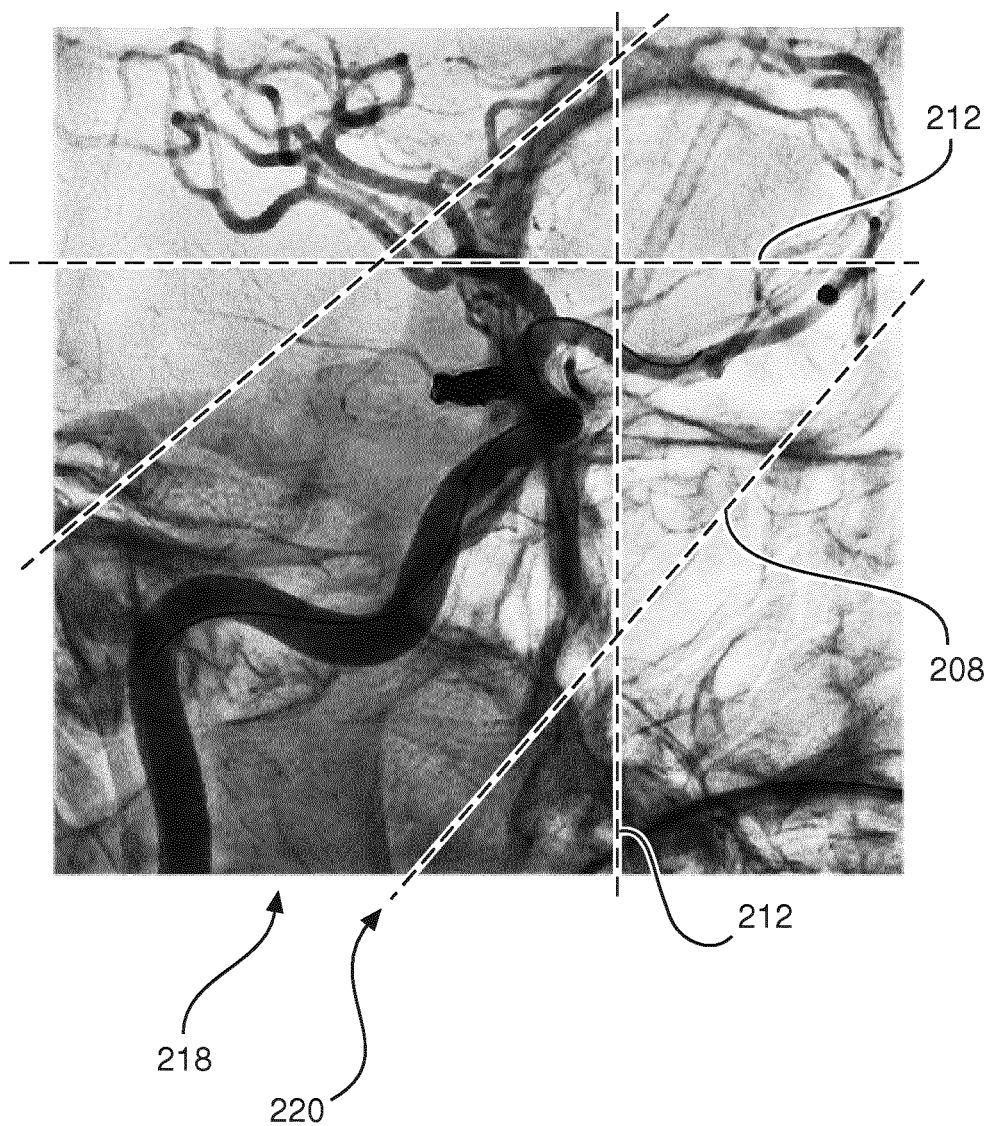
FIG. 9 shows a photographic illustration of FIG. 4.

FIG. 4 is a line drawing schematically representing the original X-ray images in FIG. 9. FIGS. 4 and 9 show a further example, where an attenuation positioning indicator 220 is displayed overlaid to an un-attenuated image region, which attenuation position indicator indicates a stored attenuation scheme. For example, the attenuation position indicator 220 comprises of a configuration showing the above-mentioned first type of line 208 and the second type of line 212, indicating the previously described wedge/shutter configuration.

For example, the attenuation position indicator 220 is displayed overlaid to the angiogram 218 or overlaid and displayed to the fluoroscopy 200.

The X-ray imaging device comprises a movable X-ray source and/or movable X-ray detector, for example shown in FIG. 1. A determined attenuation configuration of the diaphragm is stored for a determined imaging position of the X-ray source and/or the X-ray detector. The control unit 18 is configured to actuate the at least one beam-shaping element to provide the determined attenuation configuration when the X-ray source and/or the X-ray detector are moved into the determined imaging position.

In an example, a first attenuation configuration representing a first imaging mode, for example a detailed view, is provided with a minimum beam shaping of the at least one beam-shaping element and a second attenuation configuration representing a second imaging mode, for example an overview, is provided with a limitation of the X-ray beam to a selected region of interest.

The selected region may comprise a patient's vessel structure section, into which an interventional device may be inserted. The selected region may comprise at least a part of an insertion path of the interventional device.

According to a still further example, also not further shown, the control unit 18 is configured to detect a variation of the geometric relation of the X-ray imaging arrangement and/or the object under examination. The control unit is further configured to adapt the stored determined attenuation configuration of the diaphragm accordingly, and to generate adapted positioning data. The control unit 18 is further configured to supply the adapted positioning data to the at least one controllable actuator.

Figure 5:
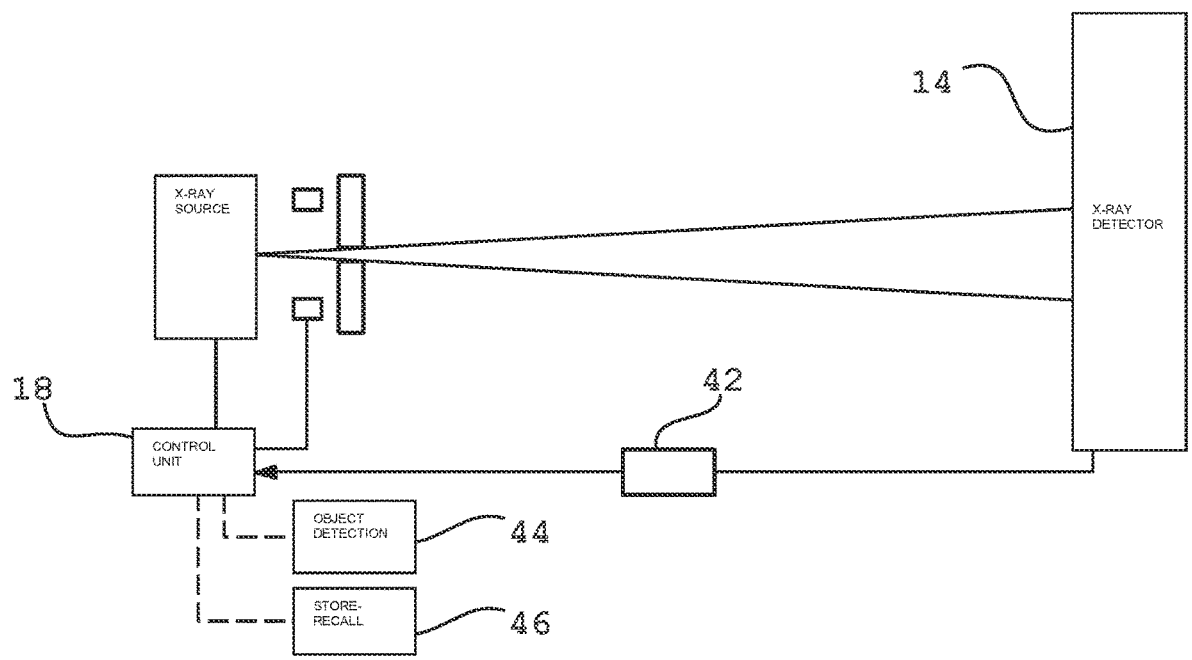
FIG. 5 shows a further schematic cross-section of an example of a medical X-ray imaging arrangement.

FIG. 5 shows a further example, where the control unit 18 comprises an image processor 42 that is configured for object detection in a provided sequence of images for the detection of the variation of the geometric relation. The control unit 18 comprises a heuristic module with a number of heuristic layers containing different scenarios. The different scenarios comprise predetermined activatable measures affiliated with the recall of stored positioning data (see also FIG. 7).

The heuristic layers may comprise a plurality of rules for different cases of change between the situation when the positioning data was stored and the situation when positioning data is recalled. The activatable measures affiliated with the recall of stored positioning may relate to different strategic approaches, for example a conservative approach and a more elaborate motion compensation strategy. For example:

In case of change in table position, i.e. object support position, the conservative approach provides to disable the recall. The elaborate approach provides to restore the table position to the store-situation and to recall the stored positioning data.

In case of a change in X-ray imaging arrangement position, e.g. a change of a C-arch position to a position that does not match any imaging position stored in the memory unit, the conservative approach provides to disable the recall. The elaborate approach provides to restore the X-ray imaging arrangement position to the stored imaging position and to recall the stored corresponding positioning data and actuate the beam-shutter elements accordingly.

In case of a change in field of view, the conservative approach provides to disable the recall of the stored positioning data if a beam-shaping element, e.g. a shutter, is outside the current field of view. The elaborate approach provides to adapt shutters that are outside the current view and to align them with an appropriate image border and to use these as positioning data.

The type of strategy depends on the type of clinical procedure.

Another heuristic approach is to differentiate between different imaging modes, for example between fluoroscopic detailed view mode and overview angiogram mode. For example, in the fluoroscopic detailed view mode, a determined attenuation configuration is applied, and in the overview angiogram mode, the at least one beam-shaping element is removed. In case different imaging positions were stored for the detailed view mode and angiogram mode, these positions can be recalled and reset accordingly.

According to a further example, also shown in combination with FIG. 5 as an option, the control unit 18 comprises an image detection module 44 to detect predetermined elements in the image data relating to predetermined interventional procedures. The control unit 18 further comprises a store-recall activation module 46 to activate storing and recalling of an attenuation configuration depending on the image content and activated imaging mode.

It is noted that the image detection module 44 and the store-recall activation module 46 may be provided in combination with the image processor 42, and also without the image processor 42, for example when the image data is provided otherwise.

In an example, the X-ray imaging device is provided as a bi-plane system with two source detector pairs. A store-and-recall functionality may be provided for each source detector pair separately (not further shown).

Figure 6:
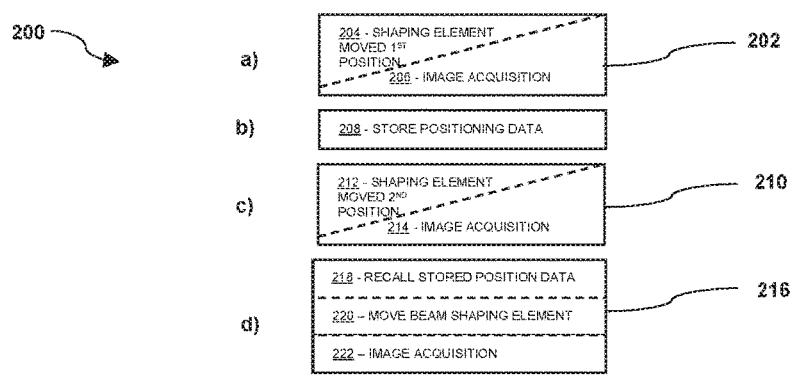
FIG. 6 shows basic steps of an example of a method for X-ray image acquisition.

In FIG. 6, a method 200 for X-ray image acquisition is shown with basic steps, for example comprising the following steps:

In a first step 202, at least one movable X-ray beam-shaping element of an adjustable X-ray beam diaphragm of an X-ray beam manipulator device of a medical X-ray imaging arrangement is moved into a first position of a first attenuation configuration. Further, X-ray image data is acquired in a first imaging mode, for example a detailed view mode for acquiring fluoroscopy data. The moving may be provided as a first sub-step 204 of the first step, and the acquisition as a second sub-step 206.

As a second step 208, the positioning data of the position of the at least one beam-shaping element is stored in a memory unit.

In a third step 210, at least one movable X-ray beam-shaping element is moved into a second position of a second attenuation configuration, and X-ray image data is acquired in a second imaging mode, for example an overview mode for acquiring an angiogram. The moving can also be referred to as first sub-step 212 of the third step 210, and the X-ray image data acquisition may be referred to as second sub-step 214 of the third step 210.

As a fourth step 216, it is provided to recall and supply the stored positioning data to a control unit for activating the controllable actuator and for moving the at least one movable X-ray beam-shaping element into the first position of the first attenuation configuration, and acquire X-ray image data in the first imaging mode. The recalling may be referred to as first sub-step 218 of the fourth step, the moving of the X-ray beam-shaping element may be referred to as second sub-step 220 and the X-ray imaging acquisition as a third sub-step 222.

The first step 202 is also referred to as step a), the second step 208 as step b), the third step 210 as step c) and the fourth step 216 as step d).

Figure 7:
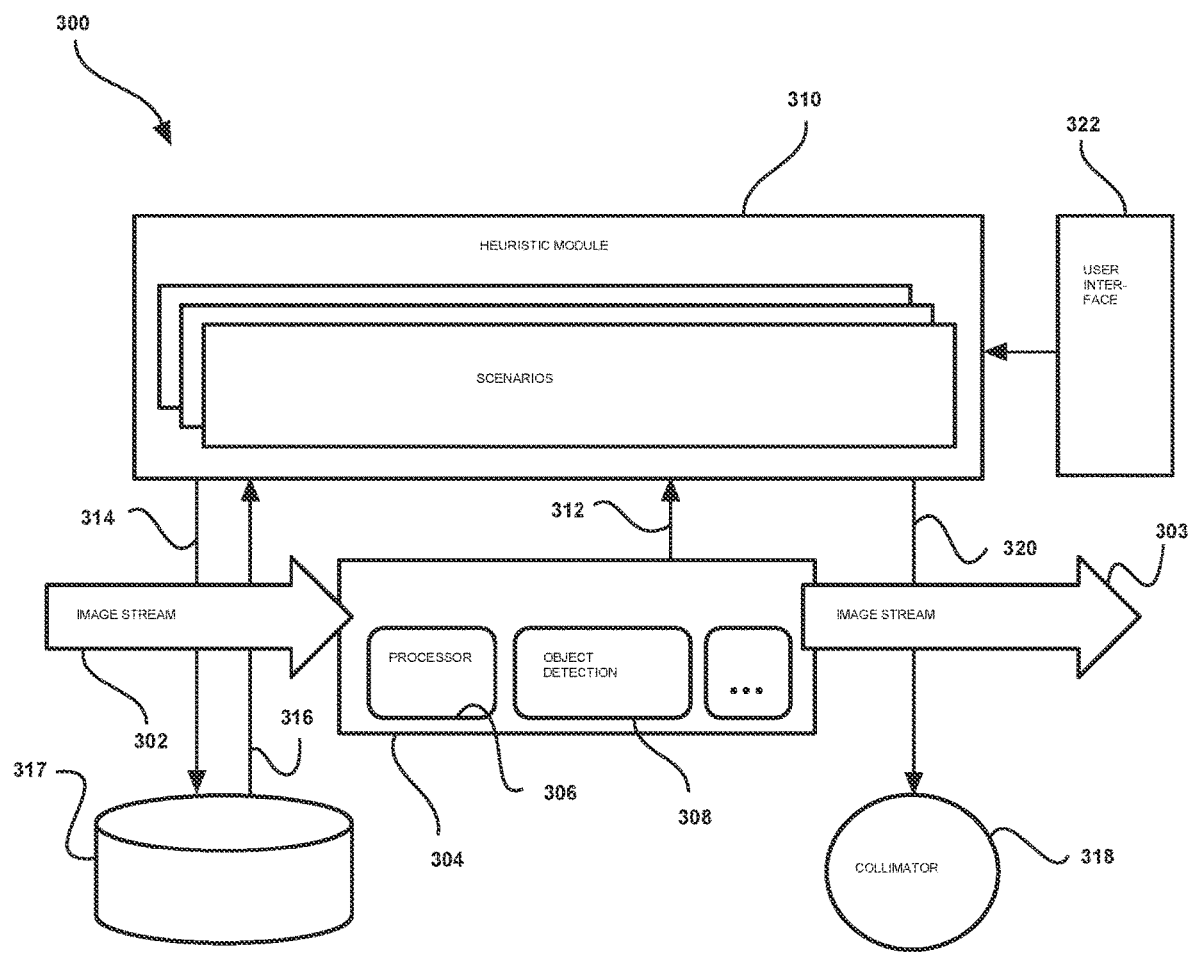
FIG. 7 shows a further diagram of an example of X-ray imaging.

FIG. 7 shows an example of a scheme 300 of a possible implementation of a shutter and wedge store-and-recall functionality. A first horizontal arrow 302 indicates an image stream, for example provided by the detector. A second horizontal arrow 303 indicates an image stream to a display. The image stream enters an image processor 304 with a first image-processing module 306, which relates to improvement of X-ray image quality. A second frame 308 indicates an object detection module. A region of interest is supplied to a heuristic module 310 comprising heuristic layers containing different scenarios. The provision of the region of interest is indicated with an arrow 312. A first arrow 314 from the heuristic module 310 leads to a data storage 317, or memory, and a second arrow 316 leads from the data storage 317 back to the heuristic module 310. The first arrow 314 indicates a STORE-function and the second arrow 316 indicates a RECALL-function. Further, commands are provided from the heuristic module 310 to a collimator 318, wherein an arrow 320 indicates the provision of the commands for the collimator, i.e. for the X-ray beam manipulator device. Still further, a user interface 322 is indicated, e.g. for entering commands to the heuristic module 310.

The heuristic layers may contain knowledge of the specific application scenario and may steer the whole process. This takes into account direct user request, for example via the user interface 322, and/or a suggested region of interest from the image processing pipeline below the heuristic layer module. It also manages the store-and-recall of collimation configurations based on evaluating a set of rules, and finally sends the necessary commands to the collimator device 318. This structure allows for both manual and fully automatic store-and-recall functionality.

As an example, fully automatic performance may be provided by applying smart image processing combined with heuristics. As an example, an automatic use case is provided for the coiling example described above. For such purpose, robust image processing functions for detecting wires and folded coils are assumed. During fluoroscopy guided coiling, the clinical user has a detailed view on the situation. Once a wire and folded coil is detected by the image processing, a region of interest ROI is computed by the software, containing these detected objects and leaving the insertion path open. Shutters and wedges are positioned automatically around this region of interest, and this collimation configuration is stored. The heuristic layer takes care of this. When the first coil is completely in the aneurism, the clinical user presses on the exposure paddle to create an angiogram-overview-run in order to check the blood flow. According to a further rule, the shutters and wedges are removed automatically from the image. After this check, the clinical user may continue with placing the second coil under fluoroscopy again in detailed view mode. The image processing detects the coil again an when the table position is not changed, for example as rule no. 1, C-arch geometry is not changed, for example as rule no. 2, and field of view is also not changed, as rule no. 3, and the previously stored collimation configuration is automatically recalled.

In a further example, a bi-plane X-ray system has both a frontal and lateral shutter and wedge store-and-recall function.

Shutter and wedge store-and-recall can be provided for more than one setting per radiation type. It is possible to store-and-recall multiple collimation configurations per radiation type.

A further example provides coupling of shutter and wedge store-and-recall with the existing position store-and-recall of the source and detector.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A medical X-ray imaging arrangement for use during an interventional procedure, comprising:
an X-ray source;
an X-ray detector;
an X-ray beam manipulator device;
a processor; and
a memory unit;
wherein the X-ray source and the X-ray detector are movable so as to achieve different imaging positions,
wherein the X-ray beam manipulator device comprises an adjustable X-ray beam diaphragm provided between the X-ray source and the X-ray detector, said beam diaphragm comprising at least one movable X-ray beam-shaping device and at least one controllable actuator for moving the at least one beam-shaping device according to positioning data provided by the processor,
wherein the processor is configured to determine positioning data representing positions of the at least one beam-shaping device for a configuration of the beam diaphragm for an imaging position and is configured to determine imaging configuration data corresponding to each imaging position for each of a plurality of different modes with different configurations of the beam diaphragm being determined for each of the plurality of different modes,
wherein the memory unit is configured to store the determined positioning data and the determined imaging configuration data,
wherein the processor is further configured to compare imaging configuration data corresponding to a current imaging position with the imaging configuration data stored in the memory unit; recall, from the memory unit, positioning data representing a configuration of the beam diaphragm associated with the current imaging position and a given mode, detect a variation of a geometric relation of the X-ray imaging arrangement and/or an object under examination, adapt the stored imaging configuration data in accordance with the detected variation to generate adapted imaging configuration data and activate the controllable actuator in accordance with the adapted imaging configuration data and the given mode, and
wherein the processor is further configured to provide a user interface to enable a user to activate the storing of the determined positioning data and the determined imaging configuration data and mode at a current step of the interventional procedure and to activate the recalling of positioning data from the memory unit at a subsequent step in the interventional procedure.

2. The medical X-ray imaging arrangement according to claim 1, wherein the at least one beam-shaping device is manually adjustable to achieve a user-adapted attenuation configuration; and
wherein the interface is provided for activation of a storage of positioning data for the user-adapted attenuation configuration.

3. The medical X-ray imaging arrangement according to claim 1, wherein the different imaging modes are at least partly connected with the positioning data of a particular stored beam diaphragm configuration.

4. The medical X-ray imaging arrangement according to claim 1, wherein the at least one beam-shaping device is:
a shutter that attenuates an X-ray beam with a first degree of attenuation; and/or
a wedge that attenuates an X-ray beam with a second degree of attenuation, wherein the first degree of attenuation is a different degree of attenuation than the second degree of attenuation.

5. The X-ray imaging arrangement according to one of the preceding claims, comprising:
a display device; and
an object support device;
wherein the display device is configured to display image data of the object arranged on the object support device, the image data provided by the X-ray detector.

6. X-ray imaging system according to claim 5, wherein an attenuation position indicator is displayed overlaid to an un-attenuated image region, which attenuation position indicator indicates a stored attenuation scheme.

7. The X-ray imaging arrangement according to claim 1, wherein the processor is configured for object detection in a provided sequence of images for the detection of the variation of the geometric relation; and
is configured to apply at least one of a plurality of rules relating to different scenarios; and wherein the different scenarios comprise predetermined activatable measures affiliated with stored positioning data that is recalled.

8. The X-ray imaging arrangement according to claim 5, wherein the processor is configured to detect predetermined elements in the image data relating to a predetermined interventional procedure; and
is configured to activate storing and recalling of positioning data depending on detected image content and/or an activated imaging mode.

9. A method for X-ray image acquisition during an interventional procedure, the method comprising acts of:
moving at least one movable X-ray beam-shaping device of an adjustable X-ray beam diaphragm of an X-ray beam manipulator device of a medical imaging arrangement into a first position of a first attenuation configuration; and acquiring X-ray image data in a first imaging mode of a plurality of different imaging modes;
storing positioning data of the first position of the at least one beam-shaping device and imaging configuration data including data identifying the first imaging mode in a memory unit, the storing being activated by a user through a user interface;
moving at least one movable X-ray beam-shaping device into a second position of a second attenuation configuration; and acquiring X-ray image data in a second imaging mode of the plurality of different imaging modes,
comparing imaging configuration data including data identifying which imaging mode of the plurality of different imaging modes is selected for a current imaging position with stored imaging configuration data that includes for each stored imaging position, different imaging configurations of the beam diaphragm for each of the plurality of different modes;
recalling stored positioning data for a current imaging position and a selected one of the plurality of different imaging modes and supplying the recalled positioning data to a processor for activating the controllable actuator and moving the at least one movable X-ray beam-shaping device accordingly to the recalled positioning data and the selected one of the plurality of different imaging modes, the recalling being activated by a user through the user interface;

detecting a variation of a geometric relation of the X-ray imaging arrangement and/or an object under examination;

adapting the stored imaging configuration data in accordance with the detected variation to generate adapted imaging configuration data; and acquiring X-ray image data in the selected one of the plurality of different imaging modes based on the adapted imaging configuration data and the selected one of the plurality of different imaging modes.

10. A tangible computer-readable storage-memory that is not a transitory propagating wave or signal comprising a computer program element for controlling an apparatus comprising an X-ray source and X-ray detector that are movable to achieve different imaging positions; an X-ray beam manipulator device; a processor and a user interface, wherein the X-ray beam manipulator device comprises an adjustable X-ray beam diaphragm provided between the X-ray source and the X-ray detector, said beam diaphragm comprising at least one movable X-ray beam-shaping device and at least one controllable actuator for moving the at least one beam-shaping device according to positioning data provided by the processor, wherein the processor is configured by the computer program element to determine positioning data representing positions of the at least one beam-shaping device for a configuration of the beam diaphragm for an imaging position and is configured by the computer program element to determine imaging configuration data corresponding to each imaging position for each of a plurality of different modes with different configurations of the beam diaphragm being determined for each of the plurality of different modes, wherein the processor is configured by the computer program element to store in the memory the determined positioning data and the determined imaging configuration data, wherein the processor is further configured by the computer program element to compare imaging configuration data corresponding to a current imaging position with the imaging configuration data stored in the memory; recall, from the memory, positioning data representing a configuration of the beam diaphragm associated with the current imaging position and a given mode, detect a variation of a geometric relation of the X-ray imaging arrangement and/or an object under examination, adapt the stored imaging configuration data in accordance with the detected variation to generate adapted imaging configuration data, and activate the controllable actuator in accordance with the adapted imaging configuration data and the given mode, and wherein the processor is further configured to provide the user interface to enable a user to activate the storing of the determined positioning data and the determined imaging configuration data and mode at a current step of the interventional procedure and to activate the recalling of positioning data from the memory at a subsequent step in the interventional procedure.

11. A tangible computer readable storage medium that is not a transitory propagating wave or signal having stored computer readable program code for operating on a computer for performing a method for X-ray image acquisition during an interventional procedure, the method comprising acts of:

moving at least one movable X-ray beam-shaping device of an adjustable X-ray beam diaphragm of an X-ray beam manipulator device of a medical imaging arrangement into a first position of a first attenuation configuration; and acquiring X-ray image data in a first imaging mode of a plurality of different imaging modes;

storing positioning data of the first position of the at least one beam-shaping device and imaging configuration data including data identifying the first imaging mode in a memory unit, the storing being activated by a user through a user interface;

moving at least one movable X-ray beam-shaping device into a second position of a second attenuation configuration; and acquiring X-ray image data in a second imaging mode of the plurality of different imaging modes, comparing imaging configuration data including data identifying which imaging mode of the plurality of different imaging modes is selected for a current imaging position with stored imaging configuration data that includes for each stored imaging position, different imaging configurations of the beam diaphragm for each of the plurality of different modes;

recalling stored positioning data for a current imaging position and a selected one of the plurality of different imaging modes, detecting a variation of a geometric relation of the X-ray imaging arrangement and/or an object under examination, adapting the stored imaging configuration data in accordance with the detected variation to generate adapted imaging configuration data, supplying the adapted imaging configuration data to a processor for activating the controllable actuator and moving the at least one movable X-ray beam-shaping device accordingly to the recalled positioning data and the selected one of the plurality of different imaging modes, the recalling being activated by a user through the user interface; and acquiring X-ray image data in the selected one of the plurality of different imaging modes based on the recalled positioning data and the selected one of the plurality of different imaging modes.

* * * * *